(12) United States Patent
Lubock et al.

(10) Patent No.: US 10,660,648 B2
(45) Date of Patent: *May 26, 2020

(54) VASCULAR OCCLUSION DEVICES AND METHODS

(71) Applicant: Inceptus Medical, LLC, Aliso Viejo, CA (US)

(72) Inventors: Paul Lubock, Monarch Beach, CA (US); Richard Quick, Mission Viejo, CA (US); Robert Rosenbluth, Laguna Niguel, CA (US); Brian J. Cox, Laguna Niguel, CA (US)

(73) Assignee: Inceptus Medical, LLC, Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/452,419

(22) Filed: Jun. 25, 2019

(65) Prior Publication Data

US 2019/0307464 A1    Oct. 10, 2019

Related U.S. Application Data

(63) Continuation of application No. 15/904,126, filed on Feb. 23, 2018, now Pat. No. 10,376,267.

(60) Provisional application No. 62/463,498, filed on Feb. 24, 2017, provisional application No. 62/507,641, filed on May 17, 2017.

(51) Int. Cl.
   *A61B 17/12*       (2006.01)
   *A61B 17/00*       (2006.01)

(52) U.S. Cl.
   CPC .... *A61B 17/12172* (2013.01); *A61B 17/1214* (2013.01); *A61B 17/12109* (2013.01);
   (Continued)

(58) Field of Classification Search
   CPC ........ A61B 17/12172; A61B 17/12109; A61B 17/1214; A61B 17/12036; A61B 17/12177; A61B 17/12122
   See application file for complete search history.

(56) References Cited

U.S. PATENT DOCUMENTS

| 3,088,363 A | 5/1963 | Sparks |
| 4,719,837 A | 1/1988 | McConnell et al. |

(Continued)

FOREIGN PATENT DOCUMENTS

| CN | 101687088 A | 3/2010 |
| CN | 102119040 A | 7/2011 |

(Continued)

OTHER PUBLICATIONS

European Search Report and Written Opinion for European App. No. 12801855, completed Dec. 17, 2014, 7 pages.

(Continued)

*Primary Examiner* — Katrina M Stransky
(74) *Attorney, Agent, or Firm* — Perkins Coie LLP

(57) ABSTRACT

A vascular occlusion device includes a braided filament mesh structure defining a longitudinal axis. The mesh structure has a relaxed configuration in which it has an axial array of radially-extending occlusion regions, each of which has a proximal side and a distal side meeting at a peripheral edge, the sides of each occlusion region forming a first angle relative to the longitudinal axis. Each occlusion region is axially separated from the adjacent occlusion region by a reduced-diameter connecting region. The mesh structure is radially compressible to a compressed state in which it is deployed intravascularly to a target site through a catheter. Upon deployment, the device radially expands to a constrained configuration in which the peripheral edges of the occlusion regions engage the vascular wall, and the sides of the occlusion regions form a second angle relative to the longitudinal axis that is smaller than the first angle.

16 Claims, 10 Drawing Sheets

(52) U.S. Cl.
CPC ... *A61B 17/12036* (2013.01); *A61B 17/12113* (2013.01); *A61B 17/12122* (2013.01); *A61B 17/12177* (2013.01); *A61B 2017/00526* (2013.01); *A61B 2017/12054* (2013.01)

(56) References Cited

U.S. PATENT DOCUMENTS

| | | |
|---|---|---|
| 4,881,444 A | 11/1989 | Krauland |
| 4,885,973 A | 12/1989 | Spain |
| 4,916,997 A | 4/1990 | Spain |
| 5,301,596 A | 4/1994 | Huey, Jr. |
| 5,702,421 A | 12/1997 | Schneidt |
| 5,725,552 A | 3/1998 | Kotula et al. |
| 5,733,294 A | 3/1998 | Forber et al. |
| 5,741,332 A | 4/1998 | Schmitt |
| 5,749,858 A | 5/1998 | Cramer |
| 5,800,525 A | 9/1998 | Bachinski et al. |
| 5,861,003 A | 1/1999 | Latson et al. |
| 5,944,738 A | 8/1999 | Amplatz et al. |
| 5,974,938 A | 11/1999 | Lloyd |
| 5,976,174 A | 11/1999 | Ruiz |
| 6,254,571 B1 | 7/2001 | Hart |
| 6,331,184 B1 | 12/2001 | Abrams |
| 6,346,117 B1 | 2/2002 | Greenhalgh |
| 6,375,668 B1 | 4/2002 | Gifford et al. |
| 6,458,139 B1 | 10/2002 | Palmer et al. |
| 6,468,303 B1 | 10/2002 | Amplatz et al. |
| 6,511,492 B1 | 1/2003 | Rosenbluth et al. |
| 6,554,849 B1 | 4/2003 | Jones et al. |
| 6,635,068 B1 | 10/2003 | Dubrul et al. |
| 6,893,458 B2 | 5/2005 | Cox et al. |
| 6,932,830 B2 | 8/2005 | Ungs |
| 6,994,092 B2 | 2/2006 | van der Burg et al. |
| 7,048,014 B2 | 5/2006 | Hyodoh et al. |
| 7,069,835 B2 | 7/2006 | Nishri et al. |
| 7,128,073 B1 | 10/2006 | van der Burg et al. |
| 7,313,505 B2 | 12/2007 | Brown |
| 7,500,345 B2 | 3/2009 | Kish |
| 7,727,189 B2 | 6/2010 | VanTassel et al. |
| 7,922,732 B2 | 4/2011 | Mazzocchi et al. |
| 8,034,061 B2 | 10/2011 | Amplatz et al. |
| 8,246,641 B2 | 8/2012 | Osborne et al. |
| 8,261,648 B1 | 9/2012 | Marchand et al. |
| 8,361,138 B2 | 1/2013 | Adams |
| 8,398,670 B2 | 3/2013 | Amplatz et al. |
| 8,430,012 B1 | 4/2013 | Marchand et al. |
| 8,454,633 B2 | 6/2013 | Amplatz et al. |
| 8,534,176 B2 | 9/2013 | Giszter et al. |
| 8,641,777 B2 | 2/2014 | Strauss et al. |
| 8,747,432 B1 | 6/2014 | Janardhan et al. |
| 8,758,389 B2 | 6/2014 | Glimsdale |
| 8,764,787 B2 | 7/2014 | Ren |
| 8,820,207 B2 | 9/2014 | Marchand et al. |
| 8,821,529 B2 | 9/2014 | Kariniemi et al. |
| 8,826,791 B2 | 9/2014 | Thompson et al. |
| 8,833,224 B2 | 9/2014 | Thompson et al. |
| 8,852,205 B2 | 10/2014 | Brady et al. |
| 8,961,556 B2 | 2/2015 | Amplatz et al. |
| 9,039,724 B2 | 5/2015 | Amplatz et al. |
| 9,078,658 B2 | 7/2015 | Hewitt et al. |
| 9,179,899 B2 | 11/2015 | Freudenthal |
| 9,179,920 B2 | 11/2015 | Ren |
| 9,259,237 B2 | 2/2016 | Quick et al. |
| 9,528,205 B2 | 12/2016 | Thompson et al. |
| 9,681,876 B2 | 6/2017 | Cragg et al. |
| 9,743,918 B2 | 8/2017 | Amplatz et al. |
| 9,765,457 B2 | 9/2017 | Tahara et al. |
| 9,770,232 B2 | 9/2017 | Amin et al. |
| 9,844,382 B2 | 12/2017 | Aboytes et al. |
| 9,861,346 B2 | 1/2018 | Callaghan |
| 9,861,467 B2 | 1/2018 | Cully et al. |
| 9,913,652 B2 | 3/2018 | Bridgeman et al. |
| 9,994,980 B2 | 6/2018 | Quick |
| 10,376,267 B2 * | 8/2019 | Lubock ............ A61B 17/12172 |
| 2002/0072765 A1 | 6/2002 | Mazzocchi et al. |
| 2002/0123802 A1 | 9/2002 | Snyders |
| 2002/0165572 A1 | 11/2002 | Saadat |
| 2003/0139802 A1 | 7/2003 | Wulfman et al. |
| 2003/0181942 A1 | 9/2003 | Sutton et al. |
| 2003/0187473 A1 | 10/2003 | Berenstein et al. |
| 2003/0204249 A1 | 10/2003 | Letort |
| 2004/0073243 A1 | 4/2004 | Sepetka et al. |
| 2004/0176798 A1 | 9/2004 | Epstein et al. |
| 2004/0215167 A1 | 10/2004 | Belson |
| 2004/0215230 A1 | 10/2004 | Frazier et al. |
| 2004/0254633 A1 | 12/2004 | Rapaport et al. |
| 2005/0113861 A1 | 5/2005 | Corcoran et al. |
| 2005/0119668 A1 | 6/2005 | Teague et al. |
| 2005/0137692 A1 | 6/2005 | Haug et al. |
| 2005/0228434 A1 | 10/2005 | Amplatz et al. |
| 2005/0267493 A1 | 12/2005 | Schreck et al. |
| 2005/0283224 A1 | 12/2005 | King |
| 2006/0129222 A1 | 6/2006 | Stinson |
| 2006/0247680 A1 | 11/2006 | Amplatz et al. |
| 2006/0265054 A1 | 11/2006 | Greenhalgh et al. |
| 2006/0293706 A1 | 12/2006 | Shimon |
| 2007/0005103 A1 | 1/2007 | Schaeffer |
| 2007/0027534 A1 | 2/2007 | Bergheim et al. |
| 2007/0093744 A1 | 4/2007 | Elmaleh |
| 2007/0106311 A1 | 5/2007 | Wallace et al. |
| 2007/0118165 A1 | 5/2007 | DeMello et al. |
| 2007/0129791 A1 | 6/2007 | Balaji |
| 2007/0161963 A1 | 7/2007 | Smalling |
| 2007/0185500 A1 | 8/2007 | Martin et al. |
| 2007/0208376 A1 | 9/2007 | Meng |
| 2007/0208412 A1 | 9/2007 | Elmaleh |
| 2007/0265656 A1 | 11/2007 | Amplatz et al. |
| 2008/0140110 A1 | 6/2008 | Spence |
| 2008/0200945 A1* | 8/2008 | Amplatz ............ A61B 17/0057 606/195 |
| 2008/0262472 A1 | 10/2008 | Lunn et al. |
| 2008/0275540 A1 | 11/2008 | Wen |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0112309 A1 | 4/2009 | Jaramillo et al. |
| 2009/0171386 A1 | 7/2009 | Amplatz et al. |
| 2009/0209855 A1 | 8/2009 | Drilling et al. |
| 2009/0222076 A1 | 9/2009 | Figulla et al. |
| 2009/0254172 A1 | 10/2009 | Grewe |
| 2009/0275974 A1 | 11/2009 | Marchand et al. |
| 2010/0023048 A1 | 1/2010 | Mach |
| 2010/0030244 A1 | 2/2010 | Woolfson et al. |
| 2010/0036474 A1 | 2/2010 | Bergheim |
| 2010/0076482 A1 | 3/2010 | Shu et al. |
| 2010/0114152 A1 | 5/2010 | Shukla |
| 2010/0168785 A1 | 7/2010 | Parker |
| 2010/0211046 A1 | 8/2010 | Adams et al. |
| 2010/0256723 A1 | 10/2010 | Murray |
| 2010/0305604 A1 | 12/2010 | Pah |
| 2010/0324588 A1 | 12/2010 | Miles et al. |
| 2011/0146361 A1 | 6/2011 | Davidson et al. |
| 2011/0152993 A1 | 6/2011 | Marchand et al. |
| 2011/0160742 A1 | 6/2011 | Ferrera et al. |
| 2011/0160753 A1 | 6/2011 | Bastin |
| 2011/0208234 A1 | 8/2011 | Mazzocchi et al. |
| 2012/0022639 A1 | 1/2012 | Hacohen et al. |
| 2012/0006187 A1 | 6/2012 | Emmerich |
| 2012/0143242 A1 | 6/2012 | Masters |
| 2012/0323267 A1 | 12/2012 | Ren |
| 2012/0330347 A1 | 12/2012 | Becking et al. |
| 2013/0092013 A1 | 4/2013 | Thompson et al. |
| 2013/0096606 A1 | 4/2013 | Bruchman et al. |
| 2013/0110153 A1 | 5/2013 | Wang et al. |
| 2013/0226223 A1 | 8/2013 | Spenser |
| 2013/0239790 A1 | 9/2013 | Thompson et al. |
| 2014/0005713 A1 | 1/2014 | Bowman |
| 2014/0005714 A1 | 1/2014 | Quick et al. |
| 2014/0052170 A1 | 2/2014 | Heuser et al. |
| 2014/0135810 A1 | 5/2014 | Divino et al. |
| 2014/0303667 A1 | 10/2014 | Cox et al. |
| 2014/0303719 A1 | 10/2014 | Cox et al. |
| 2014/0318354 A1 | 10/2014 | Thompson et al. |

(56) References Cited

U.S. PATENT DOCUMENTS

| | | |
|---|---|---|
| 2014/0318355 A1 | 10/2014 | Marchand et al. |
| 2014/0330299 A1 | 11/2014 | Rosenbluth et al. |
| 2014/0330305 A1 | 11/2014 | Rood et al. |
| 2014/0343602 A1 | 11/2014 | Cox et al. |
| 2014/0364897 A1 | 12/2014 | Myla |
| 2015/0005811 A1 | 1/2015 | Lubock et al. |
| 2015/0018860 A1 | 1/2015 | Quick et al. |
| 2015/0032148 A1 | 1/2015 | Golan |
| 2015/0039016 A1 | 2/2015 | Naor et al. |
| 2015/0133989 A1 | 5/2015 | Lubock et al. |
| 2015/0275408 A1 | 10/2015 | Tahara et al. |
| 2015/0374391 A1 | 12/2015 | Quick et al. |
| 2016/0015398 A1 | 1/2016 | Hewitt et al. |
| 2016/0128822 A1 | 5/2016 | Tejani |
| 2016/0151141 A1 | 6/2016 | Zimmerman |
| 2016/0206321 A1 | 7/2016 | Connor |
| 2017/0088988 A1 | 3/2017 | Thompson et al. |
| 2017/0119400 A1 | 5/2017 | Amplatz et al. |
| 2018/0028312 A1 | 2/2018 | Thill et al. |
| 2018/0105963 A1 | 4/2018 | Quick |
| 2018/0242980 A1 | 8/2018 | Lubock et al. |
| 2018/0274141 A1 | 9/2018 | Quick |

FOREIGN PATENT DOCUMENTS

| | | |
|---|---|---|
| CN | 103911744 | 7/2014 |
| DE | 102007056946 A1 | 5/2009 |
| EP | 1849440 A1 | 10/2007 |
| WO | WO-9601591 A1 | 1/1996 |
| WO | WO-9916382 A2 | 4/1999 |
| WO | WO-0027292 A1 | 5/2000 |
| WO | WO-0043062 A1 | 7/2000 |
| WO | WO-2006074032 A2 | 7/2006 |
| WO | WO-2006128193 A2 | 11/2006 |
| WO | WO-2008066881 A1 | 6/2008 |
| WO | WO-2008150346 A1 | 12/2008 |
| WO | WO-2009/014528 A1 | 1/2009 |
| WO | WO-2010006061 A2 | 1/2010 |
| WO | WO-2011027002 A2 | 3/2011 |
| WO | WO-2011057002 A2 | 5/2011 |
| WO | WO-2011057087 A1 | 5/2011 |
| WO | WO-2013028579 A1 | 2/2013 |
| WO | WO-2013074486 A1 | 5/2013 |
| WO | WO-2013104721 A1 | 7/2013 |
| WO | WO2018071880 | 4/2018 |
| WO | WO2018156962 | 8/2018 |

OTHER PUBLICATIONS

European Search Report and Written Opinion for European App. No. 12825306.9, Applicant: Inceptus Medical, LLC, dated May 28, 2015, 6 pages.
European Search Report for EP Application 12853768.5, Applicant: Inceptus Medical, LLC, dated Sep. 8, 2015, 6 pages.
European Search Report for EP Application No. 13733892, Applicant: Inceptus Medical, LLC, dated Oct. 26, 2015, 8 pages.
European Search Report for EP Application No. 13777656.3; Applicant: Inceptus Medical, LLC, dated Jan. 22, 2016, 9 pages.
International Search Report and Written Opinion for Application PCT/US12/43885, dated Dec. 26, 2012, 14 pages.
International Search Report and Written Opinion for Application PCT/US12/51502, dated Oct. 25, 2012, 11 pages.
International Search Report and Written Opinion for Application PCT/US12/67479, dated Feb. 25, 2013, 12 pages.
International Search Report and Written Opinion for Application PCT/US13/20381, dated Apr. 8, 2013, 13 pages.
International Search Report and Written Opinion for Application PCT/US13/37484, dated Sep. 12, 2013, 12 pages.
International Search Report and Written Opinion for International Application No. PCT/US2014/029210, dated Aug. 12, 2014, 15 pages.
Japanese Office Action for JP Patent Application No. 2014-527211, Applicant: Inceptus Medical, LLC, dated Aug. 1, 2016, 4 pages.
Lewin, "Medical Device Innovation in America: Tensions Between Food and Drug Law and Patent Law," Harvard Journal of Law and Technology, vol. 26, No. 1, Fall 2012, 25 pages.
Schmitz-Rode et al., "Temporary Pulmonary Stent Placement as Emergency Treatment of Pulmonary Embolism," Journal of the American College of Cardiology, vol. 48, No. 4, 2006 (5 pgs.).
Turk et al., "ADAPT FAST study: a direct aspiration first pass technique for acute stroke thrombectomy," J NeuroIntervent Surg, vol. 6, 2014, 6 pages.
Ross et al., "The Vascular Plug: A New Device for Parent Artery Occlusion," American Journal of Neuroradiology, Feb. 2007, pp. 385-386.
Gandhi et al., "The MVP Micro Vascular Plug: A new Paradigm in Peripheral Embolization," Insert to Endovascular Today, Apr. 2015, pp. 80-84.
International Search Report for International Application No. PCT/US2018/019532, filed Feb. 23, 2018; Applicant: Inceptus Medical, LLC; dated Jun. 27, 2018, 5 pages.
Written Opinion for International Application No. PCT/US2018/019532, filed Feb. 23, 2018; Applicant: Inceptus Medical, LLC; dated Jun. 27, 2018, 8 pages.
Barwad et al, "Amplatzer Vascular Plugs in Congenital Cardiovascular Malformations," Annals of Pediatric Cardiology 2013, vol. 6, Issue 2, Date of Web Publication: Jul. 20, 2013, 9 pages.
Sharafuddin et al, "Experimental Comparison with Standard Gianturco Coils," From the Department of Radiology, University of Minnesota Hospital and Clinic, 420 Delaware St, SE, Minneapolis, MN 55455; from the 1996 SCVIR annual meeting. Received Apr. 30, 1996; revision requested Jun. 6; revision received and accepted Jun. 19, 1996, 9 pages.

\* cited by examiner

VASCULAR OCCLUSION DEVICES AND METHODS

CROSS-REFERENCE TO RELATED APPLICATIONS

This application is a continuation of U.S. patent application Ser. No. 15/904,126, filed Feb. 23, 2018, titled "VASCULAR OCCLUSION DEVICES AND METHODS," which claims the benefit of U.S. Provisional Application No. 62/463,498, filed Feb. 24, 2017 and U.S. Provisional Application No. 62/507,641, filed May 17, 2017, each of which is hereby incorporated by reference in its entirety.

BACKGROUND

This disclosure relates to devices for closing a passageway in a body. The passageway may be a natural defect, one having occurred due to disease or trauma, or a healthy, but undesirable passageway. The subject matter of this disclosure includes methods for closing an opening in tissue, a body lumen, blood vessel, a hollow organ, or other body cavity. The disclosure also relates to occlusion devices and methods for minimally invasive implantation, in particular, percutaneous implantation, of expandable braided occlusion devices for closing passageways in the cardiovascular system.

The cardiovascular system is part of the larger circulatory system, which circulates fluids throughout the body. The circulatory system includes both the cardiovascular system and the lymphatic system. The cardiovascular system moves blood throughout the body, and the lymphatic system moves lymph, which is a clear fluid that is similar to the plasma in blood. The cardiovascular system consists of the heart and blood vessels (arteries, veins, and capillaries). It delivers oxygen and nutrients to the tissues and carries waste products to the organs responsible for elimination. The arteries carry blood from the heart to the rest of the body, and the veins carry blood back to the heart.

Initially open, and subsequently minimally invasive, surgical procedures were used to occlude vessels and lumens, particularly when symptoms were significant and drug therapy inadequate. These techniques, although often successful, were hampered by less than desirable morbidity and mortality rates, and many patients were excluded due to the severity and risks associated with these procedures. In clinical practice today, occlusion devices are generally delivered, in a collapsed state, percutaneously with a catheter through leg or arm vessels to the target vascular site or defect under fluoroscopic or ultrasonic guidance. Upon placement at the target site, the devices are allowed to expand, in situ, to an expanded state for implantation. Reduced morbidity and mortality risks have been observed using these percutaneously-delivered occlusion devices. Nevertheless, these devices may still suffer from potential drawbacks, including navigation difficulty through the catheter when collapsed, maintenance of device delivery flexibility sufficient to reliably navigate blood vessels through small diameter introducers, insufficient sealing of the vessel or defect, inadequate fixation of the device, subsequent reopening of initially occluded vessels, and inadequate provision for natural tissue ingrowth and healing following implantation. These drawbacks and others provide the impetus for the subject matter of this disclosure.

SUMMARY

Broadly, this disclosure relates to a medical device which, in some aspects, comprises an expandable mesh for at least partially closing a vascular defect (e.g., a fistula), occluding or blocking leakage around a previously-implanted vascular device, or closure of a healthy, but undesirable blood vessel or other bodily lumen.

In some aspects, a medical device in accordance with this disclosure comprises an expandable tubular mesh structure for at least partially closing a target site (e.g., a target vascular site), wherein the expandable mesh is fabricated from a self-expanding filamentous braid (i.e., made of metallic wire or non-metallic fibers), formed into a linear array of flexible, reconfigurable disc-like mesh occlusion regions providing between 4 to 10 mesh layers per centimeter when the device is in an unconstrained, radially expanded configuration. When the device is deployed in the target site, the mesh occlusion regions are reconfigured within a linear distance that provides a short, focal occlusion between about 0.5 cm and 2.5 cm as measured between the most distal and most proximal occlusion regions.

In some aspects, a medical device, as described herein, comprises an expandable tubular mesh structure for at least partially closing a structural vascular defect, wherein the expandable mesh structure is fabricated from self-expanding braid containing any of the materials described herein, resulting in a pore size of between about 0.05 mm and 0.50 mm, such as between about 0.10 mm and 0.30 mm. Alternatively, pore sizes in the range of about 0.10 mm to 2.0 mm may be employed. In some embodiments, the pore size may be in the range of 0.20 mm to 0.75 mm.

In some aspects, a medical device, as described herein, comprises an expandable tubular mesh structure for at least partially closing a bodily lumen, such as a blood vessel, fistula, aneurysm, a patent ductus arteriosus, the left atrial appendage of the heart, leakage paths around implants (e.g. heart valves), or other vascular embolization targets, wherein the expandable mesh is fabricated from a tubular, self-expanding or shape-memory braided mesh structure.

In some aspects, a method is described for embolizing a target luminal (e.g., vascular) site by providing an expandable mesh structure that at least partially occludes the site, wherein the device is over-sized diametrically, with respect to the site, by between about 10% and 150%. In some embodiments, the amount of over-sizing may be between about 25% and 75%.

In some aspects, a method is described for treating a vascular condition by providing an expandable mesh structure that at least partially occludes a target vascular site, such as an undesirable blood vessel, fistula, aneurysm, patent ductus arteriosus, the left atrial appendage of the heart, leakage paths around implants (e.g. heart valves), and other vascular embolization targets.

In some aspects, a method is described for treating a vascular site by providing an expandable tubular mesh structure that at least partially occludes the site, wherein the expandable mesh structure is fabricated from a self-expanding mesh of braided fibers, filaments, or wires containing at least one of the following materials: nickel-titanium alloys (e.g. Nitinol), stainless steel, alloys of cobalt-chrome, polyester, PTFE, ePTFE, TFE, polypropylene, nylon, TPE, PGA, PGLA, PLA, polyethylene (PE), high-density PE (HDPE), and ultra-high molecular weight PE (UHMWPE) (including oriented strands of UMHWPE commercially available under the tradenames "DYNEEMA" and "SPECTRA").

In some aspects, a method is described for embolizing a target vascular site, wherein the method includes delivering to the target site an expandable mesh occlusion device, and allowing the device to expand to at least partially occlude the target site, wherein the expandable mesh is fabricated from a self-expanding braided mesh with fiber diameters ranging between about 0.013 mm and 0.080 mm.

In some aspects, a method is described for embolizing a blood vessel, wherein the method includes delivering to a target site in the vessel an expandable mesh occlusion device, and allowing the device to expand so that it at least partially occludes the vessel, wherein the expandable mesh is fabricated from a self-expanding braided mesh that allows the device to expand from a compressed state having an essentially linear or tubular configuration, to an expanded or relaxed state in which it assumes a radially-expanded state comprising a plurality of axially-spaced, radially-expanded occlusion regions, i.e., a linear array of radially-expanded disc-like occlusion regions. In some embodiments, at least a portion of each of the occlusion regions forms an angle optimally between about 80° and 90° relative to the longitudinal axis of the of the device when the device is not constrained by the interior wall of the bodily lumen in which the device is deployed. This angle is decreased when the device is deployed and constrained by the endoluminal wall. The occlusion regions may then have an axially-flattened state such that each disc forms a pair of conjoined cones sharing a common base and defining a peripheral edge.

As used herein, the term "occlusion device," unless otherwise limited, shall be construed to encompass any device that is implantable in a bodily lumen for the purpose of at least partially obstructing the lumen, either by itself, or as an adjunct for embolization or tissue ingrowth. The term "bodily lumen" shall be construed as encompassing blood vessels and any other organ or structure that has a lumen or passageway that may provide a target site for occlusion.

DETAILED DESCRIPTION

Methods and apparatus are presented for the occlusion of bodily lumens, particularly vascular sites and vessels, by minimally invasive implantation, including percutaneous implantation of an expandable occlusion device. In some embodiments, the device may comprise a plurality of radially-expanded occlusion regions formed from a single tubular mesh structure, such as a braid of fine filaments (i.e., fibers or wires). In the treatment of vascular sites, the device may be delivered to the site through an elongate tubular delivery device such as a catheter or cannula, which may be inserted intravascularly through a blood vessel (such as the femoral vein or radial artery) and advanced to the target site. Typically, the device delivery and deployment procedure would be conducted under external imaging means such as fluoroscopy, x-ray, MRI or the like. Radiopaque markers may be incorporated into the occlusion device and/or the delivery device to help provide additional visibility under image guidance. Marker materials may include, for example, tungsten, tantalum, platinum, palladium, gold, iridium or other suitable materials.

Figure 1:
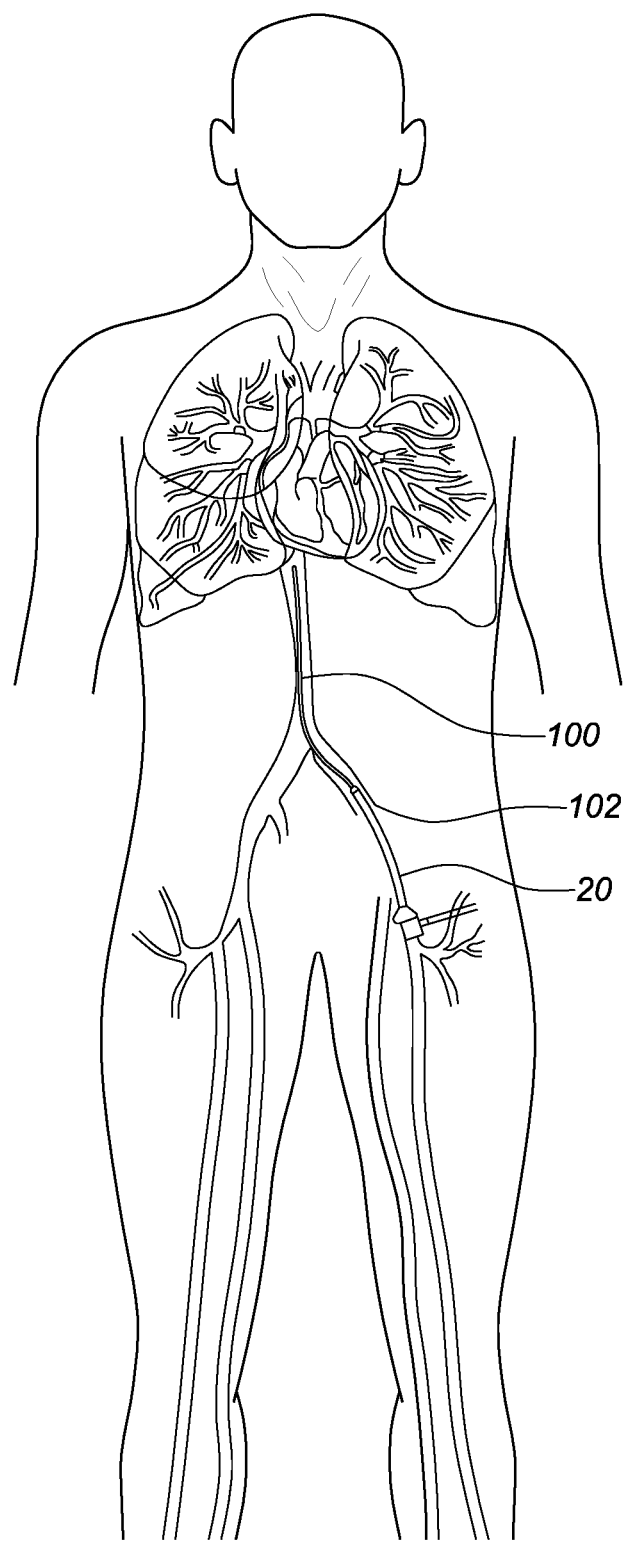
FIG. 1 is a diagrammatic view of a portion of a human cardiovascular system, showing a typical arrangement for the intravascular delivery of an implant, such as an occlusion device in accordance with this disclosure.
Figure 2:
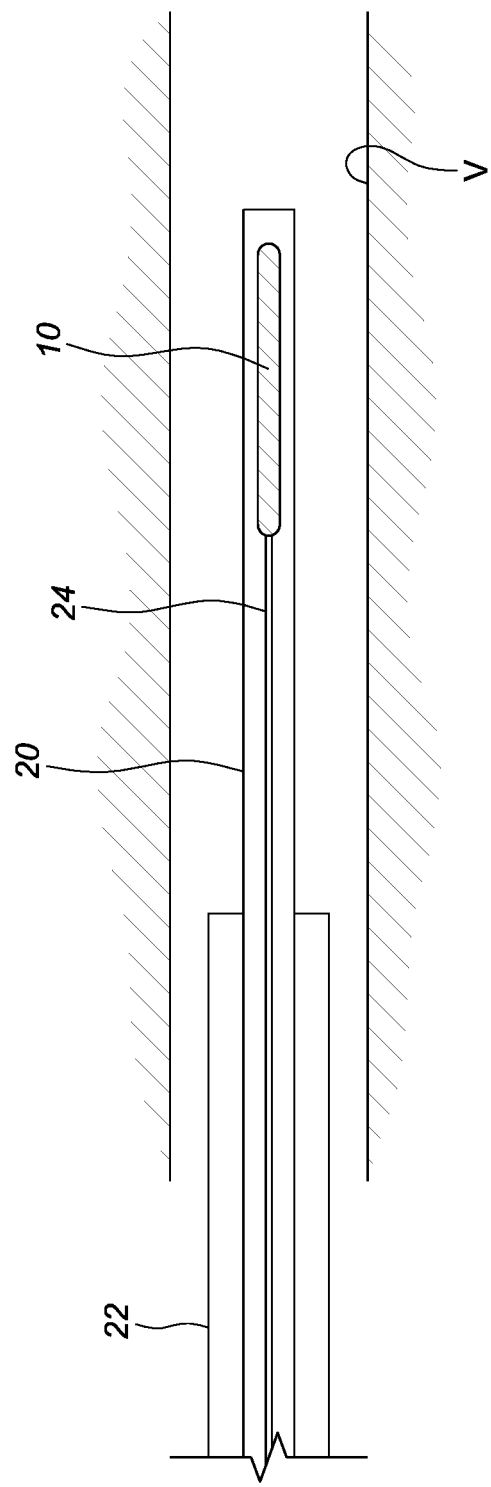
FIG. 2 is a simplified view of a device for the intravascular delivery of an occlusion device in accordance with this disclosure, showing the device being deployed intravascularly.

Occlusion devices in accordance with this disclosure are configured for intravascular delivery to a target site in a bodily lumen, particularly a vascular target site, by known techniques and procedures for intravascular deployment of vascular implants. In accordance with typical procedures of this type, a guide wire 100 capable of traversing the circulatory system is introduced into the patient through a vascular access site or puncture 102, as shown, for example, in FIG. 1. For example, an endoluminal vascular access site may be formed in a femoral artery or vein, iliac artery or vein or jugular artery or vein of a patient. This methodology of positioning a guide wire is known to physicians skilled in the art of interventional therapy. Once the guide wire 100 is positioned, the vascular access site 102 is typically dilated to permit entry of a delivery catheter 20 therethrough. A protective sheath (not shown) may be advanced to protect the vascular structure. Thereafter, the guide wire 100 may be introduced into the patient through the vascular access site 102 and advanced to the site or target of embolization. The delivery catheter 20 is then advanced over the guidewire 100 until its distal end is situated adjacent the target site. Optionally, the delivery catheter 20 may be preceded by an outer catheter or "introducer" 22, as shown in FIG. 2, through which the delivery catheter 20 is inserted. The introducer 22 may optionally be formed with a tapered distal end portion to assist in navigation through vessels; alternatively, a flexible or removable dilator (not shown) may be used, as is well-known. The delivery catheter 20 likewise can have a tapered distal end portion.

Referring still to FIG. 2, an occlusion device 10, in accordance with this disclosure, is structured, as described more fully below, so that it may be resiliently compressed from a relaxed or expanded state to a compressed state for delivery, which is how the device is shown in FIG. 2. In the compressed state, the device 10 may be substantially linear in configuration; that is, it resembles a cylinder or tube. The device 10 is connected to the distal end of a pusher element 24 by a connection element (not shown) having a detachment mechanism, which may be of any suitable type known in the art. The pusher element 24, typically in the form of, or comprising, a flexible wire, coil, multi-stranded helical wire tube or rod, is introduced into the proximal end of the delivery catheter 20 with the occlusion device 10 constrained in its compressed configuration, in which it is maintained by the constraint imposed by the inner wall surface of the delivery catheter 20. With the device 10 thus retained in a compressed state in the delivery catheter 20, it is advanced through the delivery catheter 20 by means of the pusher element 24 until it is at or near the target site in a bodily lumen, such as a blood vessel V (FIG. 2). At this point, the delivery catheter 20 is pulled proximally, freeing the occlusion device 10 from the constraint of the catheter 20, thereby allowing the occlusion device 10 to expand radially within the lumen so as to engage the endoluminal wall of the blood vessel V, as further described below, for deployment and implantation at the target site. When the device 10 is deployed at the target site, it is detached from the pusher element 24 by operation of the detachment mechanism.

If an outer catheter or introducer 22 is used (as shown, for example, in FIG. 2), the introducer 22 is advanced intravascularly until its distal end near the target site. The delivery catheter 20 is advanced distally through the introducer 22 until the distal end of the delivery catheter 20 is located at the target site. The device 10 is inserted into the proximal end of the delivery catheter 20 and pushed, by the pusher element 24, along the length of the delivery catheter up to the distal end. The delivery catheter 20 is retracted, and the device 10 is urged (e.g., by the pusher element 24) out of the distal end of the delivery catheter 20, thereby allowing the entire occlusive device 10 to expand to its functional size in an appropriate position for engagement with the walls of the target vessel or lumen at the target site. Once the device 10 is properly positioned, it is detached by the user from the pusher element 24. In some embodiments, the detachment is accomplished with minimal (preferably zero or close to zero) force being imparted to the device by the detachment mechanism to minimize movement of the device. In some embodiments, the occlusion device 10 is attached to the pusher element 24 by a tether (not shown), and the force applied needed for detachment of the tether is preferably less than 1 newton, such as, for example, 0.2-0.8 newton. Once the device has been detached, the delivery system may be withdrawn from the patient's vasculature or patient's body.

Specific embodiments of the occlusion devices disclosed herein are designed for delivery through a small intravascular delivery catheter 20 that preferably has an interior lumen diameter generally less than about 0.7 mm, known in the art as a "microcatheter." For the device to be deliverable through the microcatheter, the collapsed profile or diameter of the device must be at least slightly less than the catheter lumen. In addition, the device must have sufficient flexibility, and sufficiently little outward radial force, to allow it to track through the microcatheter without excessive friction or resistance. For a device made of braided filaments, these delivery constraints for microcatheter deliverability limit the number and size of the filaments from which the braided device is made. In addition, the number of filaments and their diameters dictate the pore structure of the device, which directly impacts how rapidly the device can occlude a vessel or lumen. The filaments and their resultant geometry in the formed structure of the device must provide sufficient strength and radial stiffness to provide for device stability when implanted to prevent distal migration and/or embolization downstream of the intended occlusion site. Accordingly, this disclosure describes the unique inter-relationships of the structural parameters of the device which allow the braided mesh structure occlusion devices described herein to achieve the desired delivery and performance characteristics.

An occlusion device in accordance with this disclosure advantageously has three inter-related performance criteria: It must be deliverable to the target site; it must remain at the target site (i.e., it does not migrate and/or embolize downstream from the target site); and it must be occlusive within the target site.

Preferred deliverability characteristics are as follows:
Compressed Diameter ($D_P$) of the device is given by the equation:
$D_P = \sqrt{N_W} * 1.14 * W/\eta$, where $N_W$ is the number of filaments forming the device, W is the diameter of each filament, and $\eta$ is the packing density of the constituent filaments.

The packing density for the filaments is the sum of the cross-sectional areas of each wire relative to the area inside the perimeter of the packed wires Collapsed tubular braided structures of round filaments have been shown to have a packing density of about 0.75.

To be efficiently deliverable through a microcatheter of inside diameter $D_C$, the device must meet the following condition:
$(D_P + 2*T_H) < D_C$, where $T_H$ is the wall thickness of the device hub, as described below.

The friction of the device passing through the microcatheter is proportional to $S_r$ and to $N_F$, where $S_r$ is the radial stiffness of each surface feature of the braided wire portion the device, and $N_F$ is the number of surface features of the radially-expanded occlusion portions of the device, as described below.

The radial stiffness $S_r$, in turn, is proportional to $N_W$ and $W^4$, and it is positively correlated to $\alpha$ and $1/R_E$, where $\alpha$ is the braid or pick angle (as described below), and $R_E$ is the edge radius of each radially-expanded occlusion region, as described below.

It is also assumed that the braid or pick angle $\alpha = F(W, N_W, D_b)$, where $D_b$ is the diameter of the mandrel on which the mesh structure is formed, as explained below.

The change in braid angle $\alpha$ for a change in braid length, B may be expressed as:
$\alpha_n = \cos^{-1}((B_n/B_i)\cos \alpha_i)$, where i indicates the initial value and n is a subsequent value These parameters drive all of the resulting device performance parameters. The goal is to use as many wires of the largest diameter possible to construct a vascular occlusion device that is occlusive and stable, while being deliverable through a microcatheter sized appropriately for the anatomical structures of concern in a particular patient.

Figure 11:
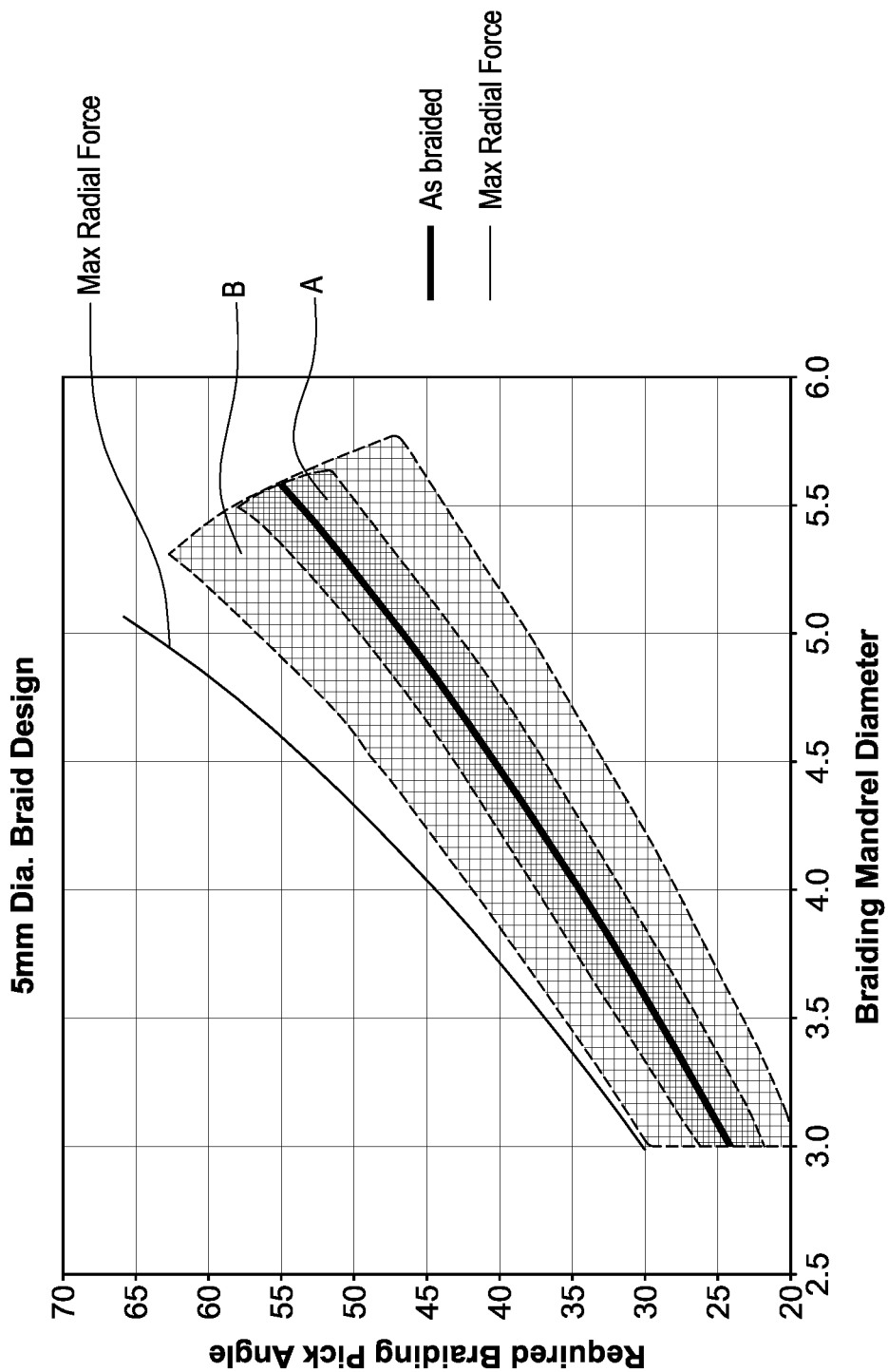
FIG. 11 shows two envelopes of braid angles for braids of 0.019 mm diameter NiTi wire with mandrels sized from 3.0 mm to 5.5 mm.
Figure 12:
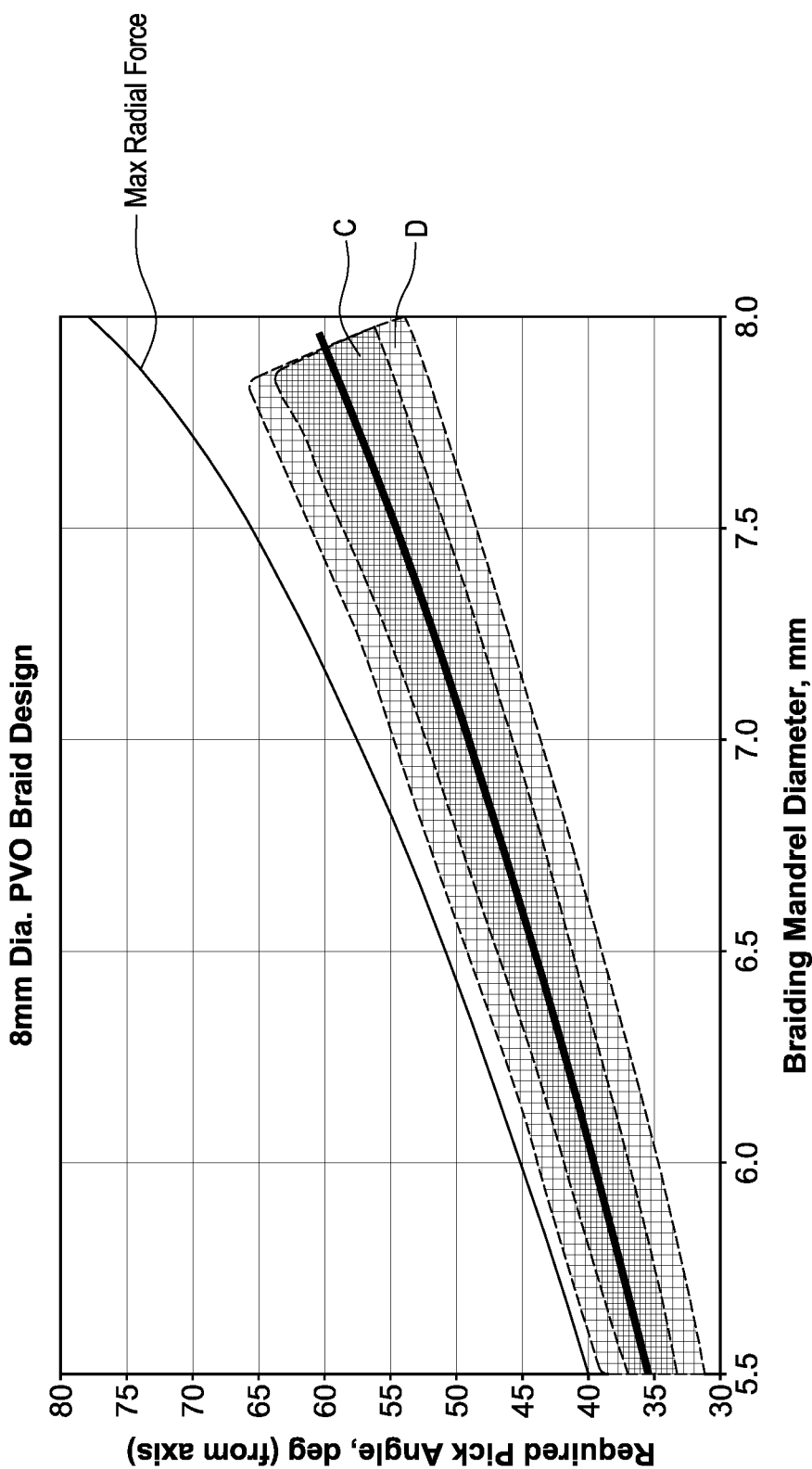
FIG. 12 shows two envelopes of braid angles for braids of 0.025 mm diameter NiTi wire with mandrels sized from 5.5 mm to 8.0 mm.

In some embodiments, to achieve the balance of the key parameters, a tubular braided wire mesh structure is formed on a mandrel using a low-tension braiding system as described herein, and the braiding parameters are set to obtain a braid or pick angle $\alpha$ in a particular range for a given wire diameter and mandrel diameter. In some embodiments, the braid angle will be within a preferred envelope a shown in FIGS. 11 and 12. FIG. 11 shows the two preferred envelopes (A and B) of braid angles for braids of 0.019 mm (0.00075") diameter NiTi wire for various mandrels sized from 3.0 mm to 5.5 mm. FIG. 12 shows the two preferred envelopes (C and D) of braid angles for braids of 0.025 mm (0.001") diameter NiTi wire with various mandrels sized from 5.5 mm to 8.0 mm. After initial forming, the braid may be secondarily formed, typically by heat treatment described herein, into a final form. In one embodiment, a braided comprising a plurality of wires with an average diameter of between about 0.017 mm and 0.021 mm, formed into a tubular mesh structure having a braid angle that lies within envelope A, can then be formed into an occlusion device with a plurality of disc-like occlusion regions, wherein the device will have both the desirable radial stiffness and the necessary deliverability through a microcatheter. In another embodiment, a braided mesh comprising a plurality of wires, each with an average diameter of between about 0.022 mm and 0.028 mm, formed into a tubular braided mesh structure having a braid angle that lies within envelope C, can then be formed into an occlusion device with a plurality of radially-expanded, disc-like occlusion regions, wherein the device will have both the desirable radial stiffness and the necessary deliverability through a catheter of a given internal diameter.

Figure 3:
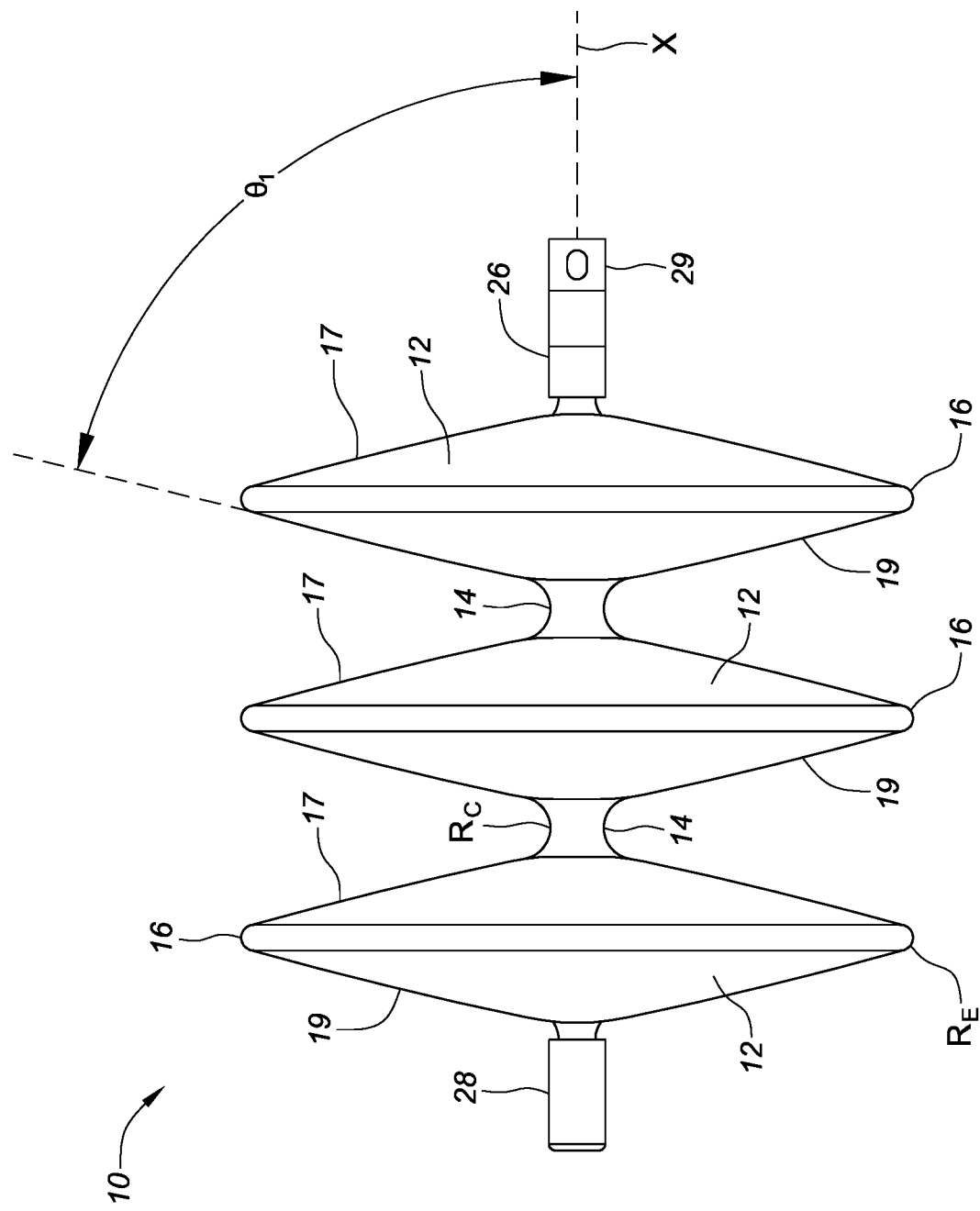
FIG. 3 is an elevational view of an occlusion device in accordance with an embodiment of this disclosure.

As shown in FIG. 3, an occlusion device 10 in accordance with an exemplary embodiment of this disclosure comprises a tubular braided structure, which has, in a relaxed or expanded state, a plurality of radially-expanded and thus radially extending occlusion regions 12, which, in some embodiments, are disc-like in configuration, as mentioned above. The occlusion regions 12 are axially spaced along the length of the device; that is, the device comprises a linear array of such occlusion regions 12. Each radially extending occlusion region 12 (hereinafter "disc," solely for the sake of brevity, and not in any limiting way) is separated from the nearest adjacent radially extending disc 12 by a tubular braided connecting region or core section 14 of reduced radius relative to the occlusion regions 12. The core sections 14 separate each adjacent pair of discs 12 by a core length that is advantageously less than about 3.0 mm, such as, for example, between about 0.5 mm and 2.5 mm.

As shown in FIG. 3, the device 10 defines a longitudinal axis X between a distal end (on the left side of the drawing) and a proximal end (on the right side of the drawing). The braided mesh structure is gathered together at each of the proximal and distal ends, where the filaments of the mesh are terminated in and retained by a proximal hub 26 and a distal hub 28, respectively. An attachment fixture 29 may advantageously be fixed to, or be integral with, the proximal hub 26, for detachable connection to a pusher element 24 by a detachment mechanism, which may advantageously include a detachable tether (not shown), as mentioned above.

Each disc 12 may advantageously be configured with a rounded peripheral edge or "apex" 16, the apices 16 of successive discs 12 being separated by a distance that may be referred to as a "pitch," as with screw threads. In some embodiments, the final, as-formed occlusive device 10 in its relaxed state may define a plurality of discs 12 with a spacing or pitch (apex to apex) distance, as shown in FIG. 3, between about 0.5 mm to 5 mm, such as, for example, between about 0.7 mm and 4.5 mm.

Figure 4:
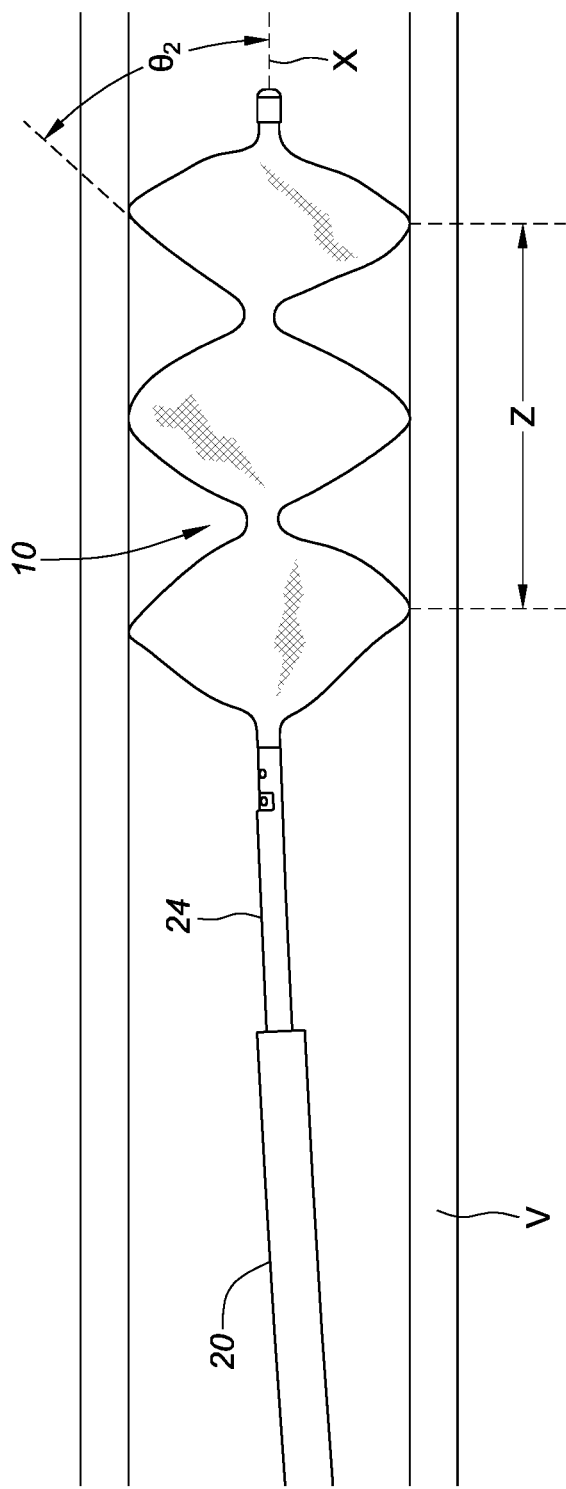
FIG. 4 is an elevation view of the occlusion device of FIG. 3, showing the device being delivered intravascularly to a target site.

Referring still to FIG. 3, in the relaxed or radially-expanded state of the device 10, each disc includes a proximal or trailing side 17 and a distal or leading side 19, meeting at the peripheral edge or apex 16. A first disc angle $\theta_1$ is defined between either the proximal side 17 or the distal side 19 of each radially-extending disc 12 and the longitudinal axis X. When the device 10 is in its relaxed or expanded state, the angle $\theta_1$ may advantageously be between 70° and 90°, although smaller angles (e.g., not greater than 85°) may be satisfactory in some embodiments, depending on the application. The disc angle decreases to a second disc angle $\theta_2$ that is smaller than the first disc angle $\theta_1$ when the device is partially constrained owing to the engagement of the peripheral edges 16 of the discs 12 with an endoluminal wall upon deployment of the device in a bodily lumen, as shown in FIG. 4. The second disc angle $\theta_2$ may be as small as 25°, although it may be beneficial for the second disc angle $\theta_2$ to be up to about 70°, as a larger angle makes the total occlusion length or "landing zone" smaller or more compact, and thus allows the physician to keep the occlusion more focal at desired location. In addition, the more compact the device and the closer the radially extending discs are to each other, the more efficiently the device may work, thereby achieving occlusion more rapidly due to subsequent layers of filament acting on the flow of blood before the flow has returned to laminar flow after being disrupted and slowed by an initial mesh layer.

The effective size of the braid may be reduced as blood passes through each layer of mesh. The pore size of the initial layer ranges between 50 microns and 500 microns. Effective pore sizes may be reduced with each subsequent layer.

The radially-extending discs 12 can have a variety of shapes with various radial cross-sections, including, but not limited to, circular (as shown), ovoid, rectangular, diamond, or arbitrarily-shaped. In addition, the discs 12 can have generally the same diameter (as shown), or different diameters. They may have similar thicknesses and spacing between them, or varied thicknesses and spacing between them. In some embodiments, the disc diameters are more than about five times their thickness at the thickest point when unconstrained. The occlusion device 10 may comprise between 2 and 8 discs in some embodiments, such as, for example, 3 to 5 discs. Each disc 12 may comprise two layers (mesh structures), that generally conform to the cross-section of the vessel or embolization site, thus spanning the lumen with a microporous flow disruptor. In some embodiments, narrow and tightly spaced discs may provide for a large number of mesh layers in close proximity, which may offer improved hemostasis. In some embodiments, when unconstrained, the occlusion device may comprise from 6 and 12 layers of mesh (each disc comprising two layers) in a linear distance of less than about 10 mm, and in less than about 25 mm in other embodiments. In some embodiments, the ratio of the linear distance between the discs and the largest disc diameter may be between about 0.7 and 2. In some embodiments, the device provides at least about 4 mesh layers per centimeter and in some embodiments, it provides from 4 to 10 mesh layers per centimeter. Optionally, the smaller diameter portions of the braid that extend from the proximal and distal discs, and that form the core portions 14 of braid between discs 12, may have a substantially uniform cylindrical shape; alternatively, the core portions 14 may have different diameters.

A short, more focal occlusion can be beneficial by keeping the occlusion zone away from branch vessels in which occlusion is not desired. In some embodiments, the device may provide a high density of mesh layers that each define a second disc angle $\theta_2$ relative to the longitudinal axis X of the occlusion device 10 that is between about 25° and 70°, preferably between 40° and 60°, when the device assumes its partially constrained configuration upon deployment at the target site, as noted above. In some embodiments the second disc angle $\theta_2$ (in the partially constrained state upon deployment) may be smaller than the first disc angle $\theta_1$ (in the relaxed or expanded state) by about 20° to 60° implanted state.

When the device 10 is deployed (implanted) at the target site, each of the discs 12 may create short, substantially circular contact regions between the peripheral edge 16 and the vessel wall, as shown in FIG. 4. Accordingly, the device 10 may provide a plurality of short and closely spaced substantially circular contact regions. In some embodiments, for example, there may be between 3 and 7 such contact regions within a linear distance of between about 1 cm and 3 cm within the blood vessel, preferably less than about 2.5 cm. In some embodiments, for example, there may be 2-4 contact regions per cm. The substantially circular contact regions are defined by the thickness of the peripheral edge 16 of each disc 12, typically less than about 2 mm, and preferably less than about 1 mm, corresponding to very short lengths along the longitudinal axis X. When the device 10 is implanted in a bodily lumen, as shown in FIG. 4, an occlusion zone Z in the lumen may be defined as the length of the lumen between the most distal and the most proximal occlusion discs 12 (as measured between their respective peripheral edges 16). Because of the small size of the contact regions (as defined above) relative to the length of the occlusion zone Z, when the device 10 is implanted, only a relatively small portion of the surface area of the occlusion zone Z is contacted by the device. In some embodiments, for example, the surface area of contact is less than about 25% of the total surface area of the occlusion zone Z. The total occlusion zone provided by the device 10 within a vessel is thus shorter and more focal than has heretofore been the norm, thereby yielding the aforementioned advantage over devices that provide relatively long occlusion zones and large vessel contact areas.

Figure 9:
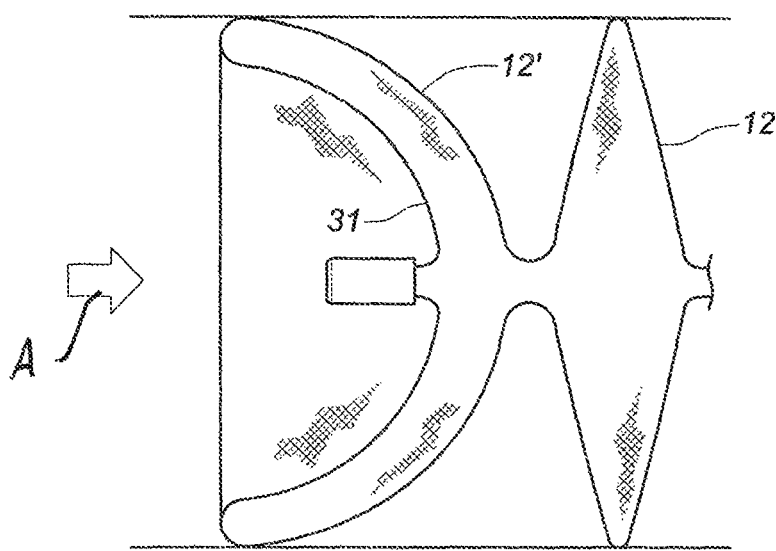
FIG. 9 is an elevation view of an occlusion device in accordance with an embodiment of this disclosure, showing the device deployed at a vascular site.

One or both of the sides of any or all of the discs may be concave or convex. In some embodiments, as shown in FIG. 9, one or more discs 12' may comprise a concavity 31 formed into a cup-like shape that faces downstream, so that blood flow and pressure in the vascular site to be embolized tends to increase the outward force against the vessel that may enhance the friction force holding the device in place, and therefore improve its stability and reduce the risk of downstream movement of the device. Alternatively, the discs may have a simple planar structure or have a small angulation so that they are thicker at the base than at the apex 16, as shown in FIG. 3. Disc and core portion diameters, shapes and dimensions vary to cover the wide range of defect sizes and shapes. In some embodiments the disc diameter may range between 2 mm and 12 mm, and the core portion diameter may range between 0.25 mm and 3 mm.

As shown in FIG. 3, in some embodiments, the peripheral edges or apices 16 of the radially-extending discs 12 of the occlusion device may advantageously have an edge radius $R_E$ of between about 0.10 mm and 0.40 mm. The core portions 14 between adjacent discs may advantageously define a core radius of $R_C$ of between about 0.25 mm and 1.0 mm. These specific ranges of disc edge and core radii for the occlusion device may provide a heretofore unknown desirable balance of deliverability and maintenance of the close spacing of the discs. Smaller radii increase the force required for delivery through a microcatheter that may be necessary for treatment of tortuous and small vessel targets. Conversely, larger disc edge radii, in particular, may result in a longer implant and less focal occlusion when implanted. A shorter device and more focal occlusion are generally desirable to the user (physician). Further, larger spacing of the discs may result in longer occlusion times.

In any of the embodiments described herein, the device components may comprise a mesh of wires, filaments, threads, sutures, fibers or the like (herein called "filaments 30") that have been configured to form a porous fabric or structure. The filaments 30 may be constructed using metals, polymers, composites, and/or biologic materials. Polymer materials may also include polymers such as polyester, polypropylene, nylon, PTFE, ePTFE, TFE, PET, TPE, PGA, PGLA, or PLA. Other suitable materials known in the art of elastic implants may be used. Metallic materials may include, but are not limited to, nickel-titanium alloys (e.g. Nitinol), platinum, cobalt-chrome alloys such as Elgiloy, stainless steel, tungsten, or titanium.

In some cases, the specific construction of a drawn filled tube wire or filament may be important to enhance the external visualization and/or maintain desired performance characteristics of the occlusion device. More specifically, it may be important to balance the stiffness, elasticity and radiopacity of the composition. In particular, for drawn filled tube filament embodiments that include an internal wire of ductile radiopaque material, such as platinum, and an outer tube of an elastic or super-elastic material such as NiTi, it can be necessary (or at least advantageous) to balance the ratio of the percent cross-sectional area of the internal wire with regard to the overall cross-sectional area of the filament. Such a ratio may be referred to as a "fill ratio." If an embodiment includes too little radiopaque internal tube material relative to the external tube material, there may not be sufficient radiopacity and visibility. On the other hand, if an embodiment includes too much internal wire material with respect to the elastic external tube, the mechanical properties of the ductile radiopaque material may overwhelm the elastic properties of the outer tube material, and the filaments may be prone to taking a set after compression, etc., resulting in permanent deformation. For some embodiments, a desired composite or drawn filled tube filament may be constructed with a fill ratio of cross-sectional area of internal fill wire to cross-sectional area of the entire composite filament of between about 10% and about 50%, more specifically between about 20% and about 40%, and even more specifically, between about 25% and about 35%.

In some embodiments, the devices for treatment of a patient's vasculature may have at least about 25% composite filaments relative to the total number of filaments, and in some embodiments such devices may have at least about 40% composite filaments relative to a total number of filaments in the device. For example, a first subset of elongate resilient filaments may comprise composite materials, each having a combination of highly radiopaque material and a high strength material, and a second subset of elongate resilient filaments may comprise mostly a high strength material. For example, the highly radiopaque material may comprise platinum, platinum alloy such as 90% platinum/10% iridium, or gold, or tantalum. The high strength material may comprise NiTi. While composite wires may provide enhanced visualization and/or mechanical characteristics, they may, in some configurations, have reduced tensile strength in comparison to NiTi wires of a similar diameter. In other configurations, depending on their diameter, the composite wires may increase the collapsed or compressed profile of the devices. Therefore, it may be beneficial to minimize the number of composite wires. Lower percentages of composite wires may not be sufficiently visible with current imaging equipment, particularly in neurovascular applications where the imaging is done through the skull. In addition, too many composite wires (or composite wires with extremely high fill ratios) may result in devices with excessive artifact on CT or MRI imaging. The described ratios and amounts of highly radiopaque material provide a unique situation for neurovascular implants where the periphery of the device is just visible under transcranial fluoroscopy, but the device imaged area is not completely obliterated (i.e., due to an artifact), as it is with conventional embolic coils that are made substantially out of platinum or platinum alloys. One manner of achieving the desired degree of radiopacity is by selecting a particular combination of fill ratio of the composite filaments and the percent of composite filaments in relation to the total number of wires. The total percent of radiopaque platinum, for example, in the braided structure may be between about 15% and 30%.

Figure 7:
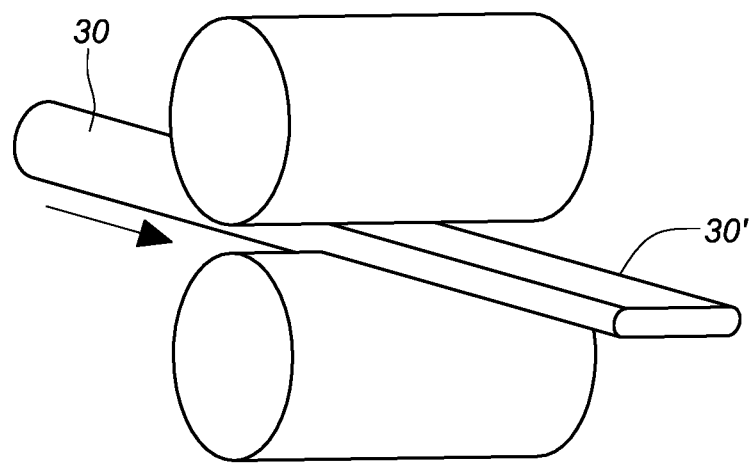
FIG. 7 shows the process of flattening a filament used in the manufacture of an occlusion device in accordance with aspects of this disclosure.

In any of the braid filaments described herein, the cross-section may be circular, ovoid, rectangular or square. In some embodiments, the filaments 30 may be formed initially with a circular cross-section, and then rolled or partially flattened to form a flattened filament 30' having a generally rectangular cross-section with rounded corners, as shown in FIG. 7. This configuration may provide improved ability to braid the desired configuration of braid angle and pore structure.

Specifically, for a given filament thickness, the larger the "pick length" (distance between filament crossings), the longer the beam length relative to the filament displacement, and the lower the stress in the filament induced by the displacement. Also, for a given pick length, the smaller the filament thickness, the larger the pick length, and the longer the beam length relative to the filament displacement, the lower the stress in the filament induced by the displacement. If a circular filament is subsequently flattened along its axis, forming two parallel planes symmetric about the filament axis, then the filament thickness will be reduced without reducing the cross-section and thus the tensile strength of the filament.

Flattening the filament requires less beam displacement to form the braid. Therefore, one can expect smaller pick length for a given filament tension. Accordingly, reducing pick length reduces the "pore" size of the weave. Also, the flattened filament is "wider" than the diameter of the circular filament, and as such, occupies more of the pore surface area for any equal pick length, further reducing pore size.

Bending stiffness is E*I, where E is the tensile modulus, and I is the polar moment of inertia of the cross-section normal to the bending axis. E is the same for both flattened (elliptical) and circular filaments. The value of I of the flattened filament is 22% that of the circular filament of the same cross-sectional area. Therefore, the flattened filament is only 22% as stiff. Under the same tensile load, the pick length would be reduced based on this factor alone. Flattening a circular filament will reduce the braided pore size due to smaller bending displacement, wider cross-section, and reduced bending stiffness.

Figure 5:
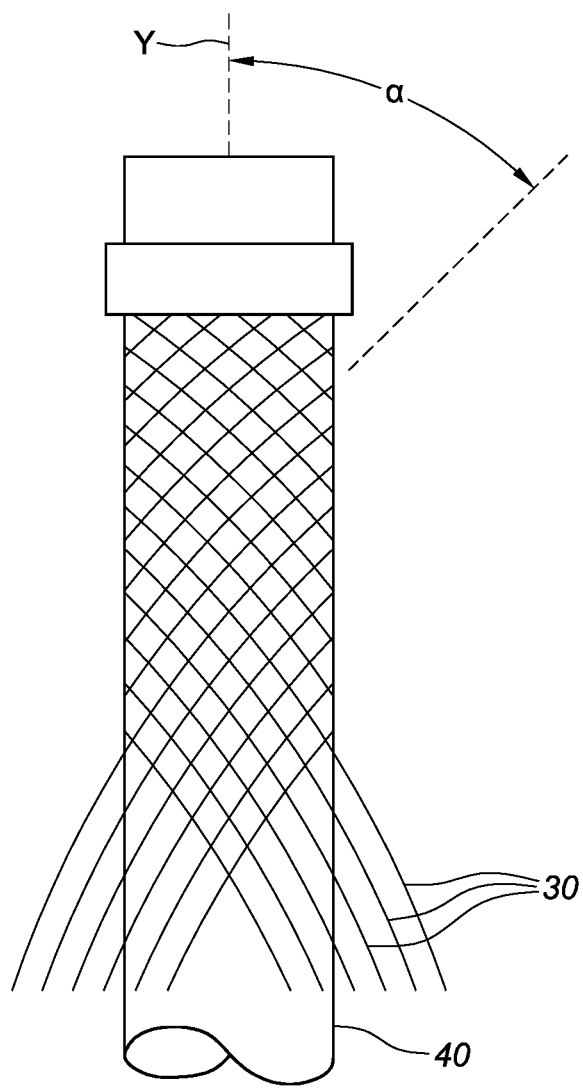
FIG. 5 is a simplified view of a portion of an apparatus for braiding the filament from which an occlusion device in accordance with aspects of this disclosure is made.
Figure 8:
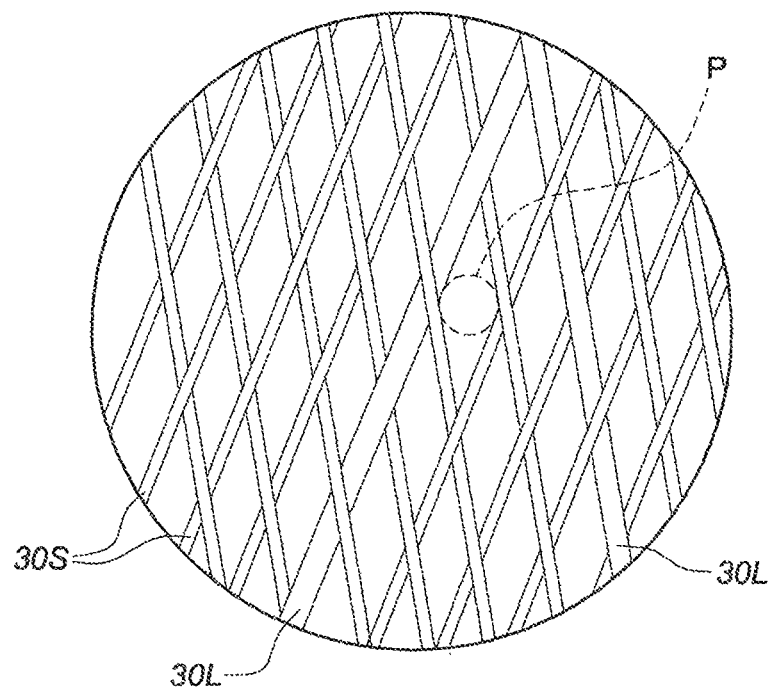
FIG. 8 is an enlarged, detailed view of the filamentous structure of an occlusion device in accordance with aspects of this disclosure.

In some embodiments, the device may comprise a braided mesh of fine filaments. In some embodiments, the braided mesh may be formed over a mandrel 40, as is known in the art of tubular braid manufacturing and shown in FIG. 5. The mesh is formed with a braid angle α relative the longitudinal axis Y of the mandrel 40. The braid angle α may be controlled by various means known in the art of filament braiding. The braids for the mesh components may have a generally constant braid angle α over the length of a component, or the braid angle α may be varied to provide different zones of pore size and radial stiffness. The "pore size" is defined as the largest circle that may be inscribed inside the diamond formed by the crossed filaments, as indicated by the dashed circle P in FIG. 8.

Figure 6:
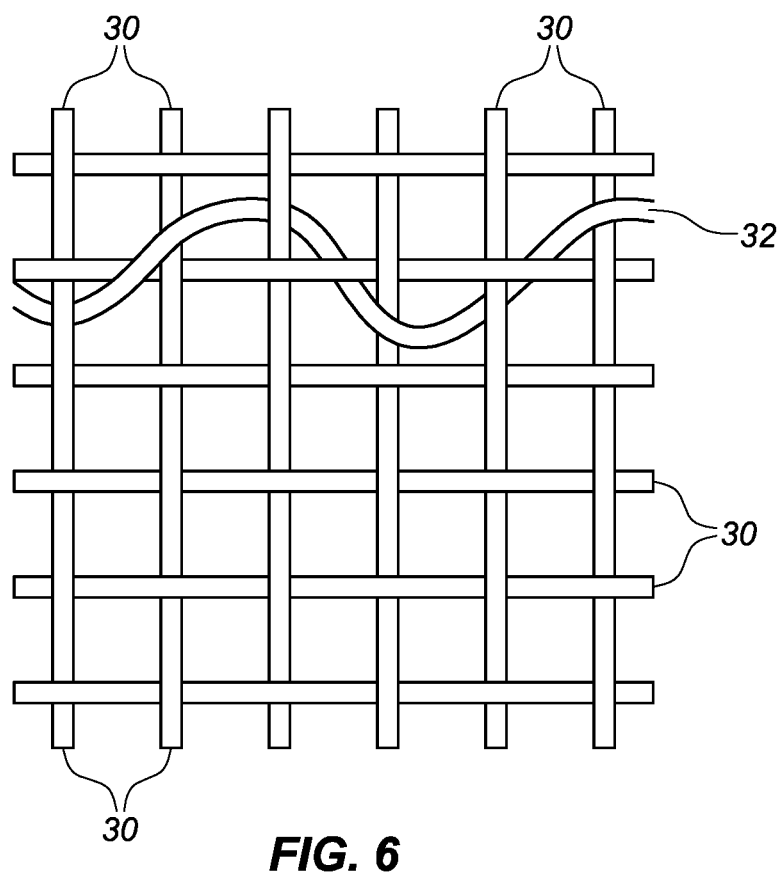
FIG. 6 is a simplified view of the filamentous structure of an occlusion device in accordance with aspects of this disclosure.

In some embodiments, as shown in FIG. 6, substantially non-structural filamentary or fibrous members 32 may be attached or interwoven into the structural filaments 30 of a portion of the device to increase a resistance to the flow of blood through the mesh structure or enhance the formation of thrombus and/or healing of the tissue around the device. In some embodiments, one or more fibers or yarns 32 may be interwoven or interlaced into the braided mesh, as shown in FIG. 6. The non-structural fibers 32 may be interlaced into the braided mesh during the braiding process or after. The non-structural fibers 32, which may be microfibers or any other suitable fibers, may be polymeric and may beneficially be more thrombogenic than the mesh filaments. The non-structural fibers 32 may include, but are not limited to, any of the materials described herein.

In some embodiments, the tubular braided filament mesh structure can be formed by a braiding machine. It may be advantageous to utilize a braiding machine that does not employ bobbins or other filament spooling and tensioning mechanisms, typical of many conventional braiders, as they make braiding of very fine filaments and mixing of different filament diameters more difficult. Low tension braiding machines can allow less filament breakage and are more amenable to mixed diameter filament braid. In some embodiments, the braided filament mesh structure can be braided using methods or devices described in one or more of: U.S. Pat. No. 8,833,224, entitled "BRAIDING MECHANISM AND METHOD OF USE"; U.S. Pat. No. 8,826,791, entitled "BRAIDING MECHANISM AND METHOD OF USE"; U.S. Pat. No. 8,261,648, entitled "BRAIDING MECHANISM AND METHOD OF USE"; U.S. Pat. No. 8,820,207, entitled "BRAIDING MECHANISM AND METHOD OF USE"; and U.S. Patent Publication No. 2014/0318354, entitled "BRAIDING MECHANISM AND METHOD OF USE". The disclosures of all of the aforementioned patents are hereby incorporated by reference herein.

Figure 10:
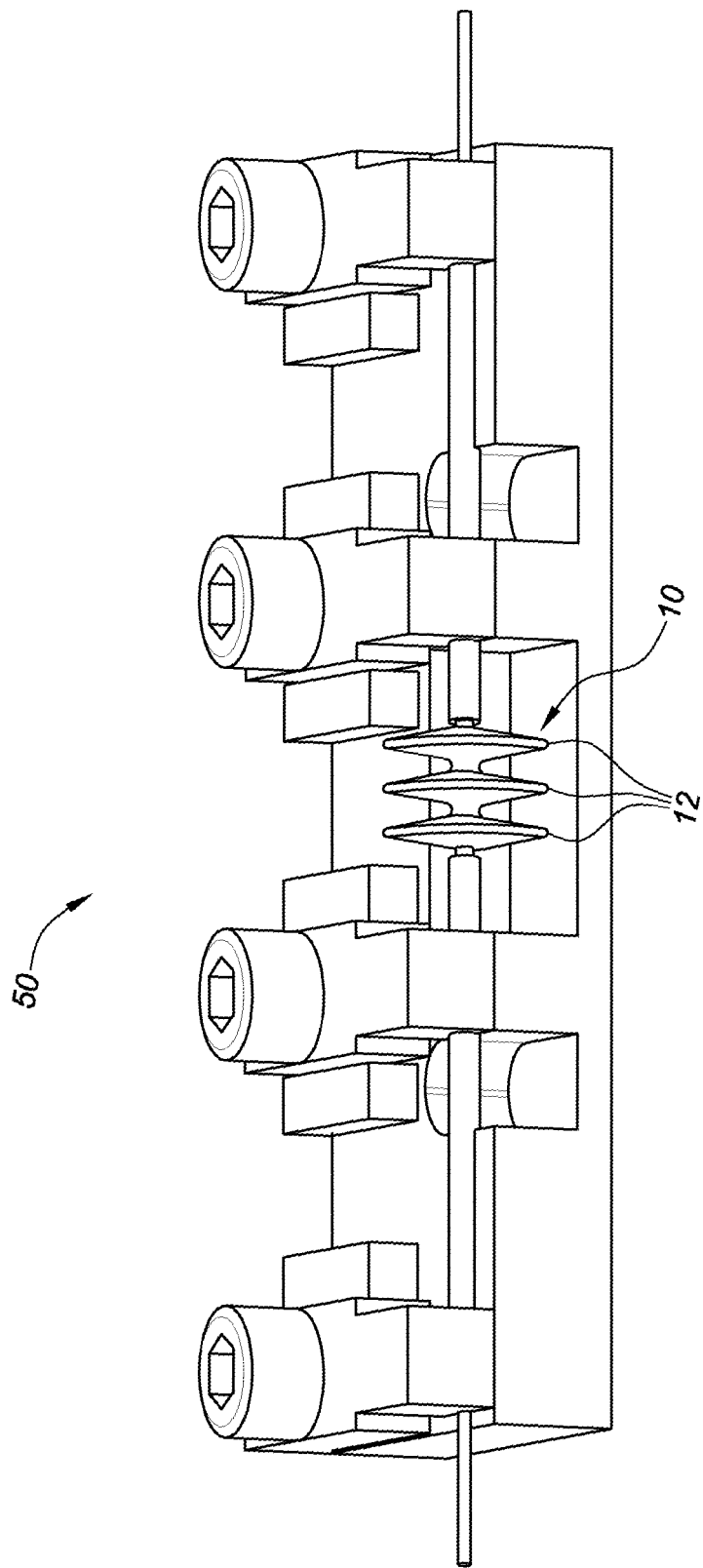
FIG. 10 shows an embodiment of a heat treatment fixture for manufacturing an occlusion device in accordance with aspects of this disclosure.

The tubular braided mesh may then be further shaped using a heat setting process. As is known in the art of heat setting nitinol wires, a fixture, mandrel or mold may be used to hold the braided tubular structure in its desired configuration, then subjected to an appropriate heat treatment, such that the resilient filaments of the braided tubular member assume or are otherwise shape-set to the outer contour of the mandrel or mold. A conventional heat treatment fixture 50 is shown in FIG. 10, in which a mesh device or component 10 is held. The fixture 50 is configured to hold the device or component in a desired shape, and the device or component is heated while so held to about 475-525° C. for about 5-30 minutes to shape-set the structure. The heat setting process may be performed in an oven or fluidized bed, as is well-known. In some embodiments, the heat setting process may be done in an inert gas environment. In some embodiments, a system for heat treating a device comprises a chamber configured to contain bath media, a container within the chamber and configured to hold the device, an air inlet gate fluidly upstream of the chamber and configured to be coupled to a gas source to flow gas into the chamber to fluidize the bath media, and a heating element between the air inlet gate and the chamber. The bath media may advantageously and optionally include sand. The gas source may comprise air, nitrogen, hydrogen, carbon monoxide, or any combination thereof. The system may further comprise thermal sensors electrically connected to a temperature regulator. In some embodiments, a system for heat treating a device comprises a chamber configured to contain bath media, and a container within the chamber and configured to hold the device. Gas flow into the chamber is provided so as to fluidize the bath media.

In some embodiments, the device can be formed at least in part from a cylindrical braid of elastic filaments. Thus, the braid may be radially constrained without plastic deformation and will self-expand on release of the radial constraint. Such a braid of elastic filaments is herein referred to as a "self-expanding braid." In accordance with the present disclosure, braids of generally smaller filaments than current occlusion devices are preferably used. In some embodiments, the thickness of the braid filaments would be less than about 0.10 mm. In some embodiments, the braid may be fabricated from wires with diameters ranging from about 0.015 mm to about 0.080 mm.

In some embodiments, the diameter of the braid filaments can be less than about 0.5 mm. In other embodiments, the filament diameter may range from about 0.01 mm to about 0.40 mm. In some embodiments, braid filaments of varying diameters may be combined in the mesh to impart different characteristics including, e.g., stiffness, elasticity, structure, radial force, pore size, occlusive ability, and/or other features. In some embodiments, larger, structural filaments may be fabricated from wires with diameters ranging from about 0.025 mm to about 0.25 mm. In some embodiments, the thickness of the smaller braid filaments would be between about 0.01 mm about 0.05 mm. The ratio of the number of small filaments to the number of large filaments may be between about 2 and 20, such as, for example, between 4 and 12. An exemplary embodiment comprising filaments of two different sizes (cross-sectional areas) is shown, for example, in FIG. 8, in which an array of larger filaments 30L is integrated into an array of smaller filaments 30S.

Prior to treatment, a device size is chosen based on the size and morphology of the site to be embolized. In general, the device is generally selected so that the diameter of its occlusion regions in the expanded state is larger than the diameter or largest dimension of the site, and, thus oversized, provides a residual radial force, lending stability to the device. When deployed in a vascular site in an over-sized and at least partially compressed state, the device will assume a constrained configuration, in which the shape of the discs 12 will be axially elongated as compared to the expanded or relaxed state of the device, thereby decreasing the disc angle relative to the longitudinal axis of the device, as described above. The device may be over-sized diametrically relative to the target vessel diameter by between about 10% and 100% in some embodiments, and preferably between about 25% and 75%. When deployed in an over-sized and thus partially compressed state, the discs assume a constrained configuration, forming a plurality of mesh layers (i.e., two for each disc 12), in which at least a portion of the external surface of each disc 12 forms the aforementioned second disc angle $\theta_2$ with respect to the longitudinal axis X of the device (which will generally correspond with the local longitudinal axis of the vascular site, e.g. blood vessel). As mentioned above, the second disc angle $\theta_2$ will typically be measurably smaller than 70°, such as, for example, between about 40° and 60° relative to the longitudinal axis X of the device. In some embodiments, the device 10 has a plurality of layers packed or configured within a linear distance that provides a short, focal occlusion zone Z of less than about 2.5 cm in length, such as, for example, between about 0.5 cm and 2.0 cm, as measured between the apices 16 of the most distal and most proximal discs 12 when the occlusion device is implanted, as shown in FIG. 4.

The shape and porosity of the device work synergistically to provide vascular occlusion and a biocompatible scaffold to promote new tissue ingrowth. These functions can be influenced by the "pore size" or "weave density" generally described as the pick count (number of interlacings) per unit length of the material. The devices in accordance with the present disclosure provide generally higher wire counts than current occlusion devices and thus smaller pore sizes, yielding improved occlusion performance, and thus may obviate the need for polymer fabric components that can increase thromboembolic risk due to clot formation, while also increasing the collapsed profile or diameter of the device. Pore sizes in the range of about 0.05 mm to 0.50 mm may be utilized. In some embodiments, the pore size may be in the range of 0.10 mm to 0.25 mm. The relatively higher wire counts provide a large number of filament or wire radial traverses of the target vessel that is being occluded. Since each disc provides two filament radial traverses from the central core portion to the apex of the disc, the total number of wire radial traverses in a device is equal to the number of filaments or wire times the number of discs times 2. In some embodiments, each radially extending occlusion region or disc defines two radial traverses for each wire, wherein the total number of radial traverses for the device is between 720 and 2000.

In any of the embodiments herein, the device 10 may contain at least one tine, barb, hook, pin or anchor (hereinafter called "barbs", not shown) that may be incorporated into the structure to help provide additional fixation of the device to the vessel wall or other tissue. The length of the barbs may be from about 0.25 to 3 mm, and preferably between about 0.5 to 2 mm.

Optionally, the occlusion device may be constructed to provide the elution or delivery of one or more beneficial drugs and/or other bioactive substances into the blood or the surrounding tissue. Optionally, the device may be coated with various polymers to enhance its performance, fixation, and/or biocompatibility. Optionally, the device may incorporate cells and/or other biologic material to promote fixation, sealing, reduction of leaks or healing. In any of the above embodiments, the device may include a drug or bioactive agent to enhance the performance of the device and/or healing of the target site and nearby tissue. In some embodiments, at least a portion of the device may include: an antiplatelet agent, including but not limited to aspirin; glycoprotein IIb/IIIa receptor inhibitors (including one or more of abciximab, eptifibatide, tirofiban, lamifiban, fradafiban, cromafiban, toxifiban, XV454, lefradafiban, klerval, lotrafiban, orbofiban, and xemilofiban), dipyridamole, apo-dipyridamole, persantine, prostacyclin, ticlopidine, clopidogrel, cromafiban, cilostazol, and/or nitric oxide. In any of the above embodiments, the device may include an anticoagulant, such as heparin, low molecular weight heparin, hirudin, warfarin, bivalirudin, hirudin, argatroban, forskolin, ximelagatran, vapiprost, prostacyclin and prostacyclin analogues, dextran, synthetic antithrombin, Vasoflux, argatroban, efegatran, tick anticoagulant peptide, Ppack, HMG-CoA reductase inhibitors, and thromboxane A2 receptor inhibitors. Device embodiments herein may include a surface treatment or coating on a portion, side surface, or all surfaces, wherein the surface treatment or coating promotes or inhibits thrombosis, clotting, healing or other embolization performance measures. The surface treatment or coating may be a synthetic, biologic or combination thereof. For some embodiments, at least a portion of a surface of the device may have a surface treatment or coating made of a biodegradable or bioresorbable material such as a polylactide, polyglycolide or a copolymer thereof. Another surface treatment or coating material which may enhance the embolization performance of a device includes a polysaccharide, such as an alginate-based material. Some coating embodiments may include extracellular matrix proteins such as ECM proteins. One example of such a coating may be Finale Prohealing coating which is commercially available from Surmodics Inc., Eden Prairie, Minn. Another exemplary coating may be Polyzene-F, which is commercially available from CeloNovo BioSciences, Inc., Newnan, Ga. In some embodiments, the coatings may be applied with a thickness that is less than about 25% of a transverse dimension of the filaments.

The terms "formed", "preformed" and "fabricated" may include the use of molds or tools that are designed to impart a shape, geometry, bend, curve, slit, serration, scallop, void, hole in the elastic, super-elastic, or shape memory material or materials used in the components of the device. These molds or tools may impart such features at prescribed temperatures or heat treatments.

An exemplary low force detachment system may comprise a mechanism for deploying an occlusion device in accordance with this disclosure as an implant in a bodily lumen, wherein the implant is delivered to a luminal site through a catheter by means of a pusher implement having a distal end to which a proximal end of the implant is detachably connected by a filamentous tether (not shown). The tether extends from a first end, through a "fenestration feature" (e.g., an eyelet or a loop) on the proximal end of the device, to a second end. The first end of the tether is connected to a tether take-up assembly in a tether control device, and the second end of the tether is releasably captured in the tether control device by a tether retention assembly that is operable to release the second end when the device is deployed. Upon release of the second end by the retention assembly, the take-up assembly withdraws the tether through the fenestration feature until the tether is free of the fenestration feature. The system may preferably detach the device instantaneously or nearly so, that is, in less than about 1 second. The system may preferably detach the device by mechanical means, but without the transmission of torque in or through the delivery catheter or pusher. In some embodiments, the system may comprise an interlocking loops detachment system where a user can disengage an occlusion device through a single action on the retraction device that preferably, only acts on the implant pusher guidewire during a retraction phase of movement, and allows for resetting of the retraction device for retraction without reinsertion of the guidewire. In one embodiment, the system may comprise an implant comprising a proximal end and a distal end with a first loop attached at its proximal end; a sheath comprising a proximal end and a distal end with a second loop attached near its distal end; a guidewire slidably disposed within the sheath having a proximal end and distal end; wherein the guidewire, when engaged through the first and second loops provides a releasable connection of the implant to the sheath that can be released by retraction of the guidewire; a handle handpiece comprising a retraction mechanism adapted to receive the proximal ends of the sheath and guidewire; the retraction mechanism comprising a finger actuator, a ratcheting device, a first spring member and second spring member; the ratcheting device comprising a rotatable lever, a gripping insert, an anvil, a guide arm and a guide ramp; wherein the first spring member biases the rotatable lever against the guidewire and the second spring member provides a biasing force against retraction of the finger actuator; wherein the gripping insert, when actuated by the finger actuator, acts on the guidewire to retract the guidewire within the sheath and release the implant.

For some embodiments, the detachment of the device from the delivery apparatus of the delivery system may be effected by the delivery of energy (e.g., electrical current, heat, radiofrequency, ultrasound, vibrational, or laser) to a junction or release mechanism between the device and the delivery apparatus.

Disclosed herein is a detailed description of various illustrated embodiments of the disclosed subject matter. This description is not to be taken in a limiting sense, but is made merely for the purpose of illustration of the general principles of such subject matter. Further features and advantages of the subject matter of this disclosure will become apparent to those of skill in the art in view of the description of embodiments disclosed, when considered together with the attached drawings.

Although several embodiments of the subject matter of this disclosure have been described in terms of particular embodiments and applications, one of ordinary skill in the art, in light of this teaching, can generate additional embodiments and modifications without departing from the spirit of or exceeding the scope of the disclosure. Accordingly, it is to be understood that the drawings and descriptions herein are proffered by way of example to facilitate comprehension of the disclosure and should not be construed to limit the scope thereof.

We claim:

1. A method for embolizing a blood vessel having an endoluminal wall defining a vascular lumen, the method comprising:
    advancing, via a pusher, an occlusion device to a target site in the vascular lumen of the blood vessel while the occlusion device is in a compressed state;
    deploying the occlusion device at the target site in the blood vessel, wherein the occlusion device includes a mesh structure defining a longitudinal axis, wherein deploying the occlusion device includes radially expanding the occlusion device from the compressed state to an expanded state, and wherein, in the expanded state—
        the occlusion device includes a plurality of radially extending regions,
        individual ones of the radially extending regions include an apex that contacts the endoluminal wall of the blood vessel,
        each of the apices has a thickness along the longitudinal axis of the occlusion device, and
        the combined thicknesses of the apices is less than about 50% of a total length of the mesh structure along the longitudinal axis;
    detaching the occlusion device from the pusher; and
    maintaining the occlusion device in the expanded state at the target site in the blood vessel at least until the vascular lumen at the vascular site is embolized to occlude blood flow through the vascular lumen.

2. The method of claim 1 wherein detaching the occlusion device from the pusher includes detaching the occlusion device from the pusher in less than about 1 second.

3. The method of claim 1 wherein detaching the occlusion device from the pusher includes releasing a tether connecting the occlusion device to the pusher.

4. The method of claim 1 wherein each of the apices has a thickness of less than about 1 mm, and wherein the plurality of radially extending regions includes at least three radially extending regions.

5. The method of claim 1 wherein, in the expanded state, the combined thicknesses of the apices is less than about 25% of a total length of the mesh structure along the longitudinal axis.

6. The method of claim 1 wherein the total length of the mesh structure is between about 0.5 cm and 2.5 cm.

7. The method of claim 1 wherein individual ones of the radially extending regions (a) are substantially symmetric about a plane extending through the apex and perpendicular to the longitudinal axis and (b) have a circular cross-sectional shape along the plane.

8. The method of claim 1 wherein—
the mesh structure is constrained by the blood vessel such that the expanded state is a partially-expanded state,
the mesh structure is further configured to radially expand to a fully-expanded state when the mesh structure is unconstrained by the blood vessel,
in the fully-expanded state, individual ones of the radially extending regions define a first angle relative to the longitudinal axis,
in the partially-expanded state, individual ones of the radially extending regions define a second angle relative to the longitudinal axis, and
the second angle is between about 20°-60° less than the first angle.

9. A method for embolizing a blood vessel having an endoluminal wall defining a vascular lumen, the method comprising:
advancing an occlusion device, in a compressed state, to a target site in the vascular lumen of the blood vessel;
deploying the occlusion device at the target site in the blood vessel, wherein the occlusion device includes a mesh structure defining a longitudinal axis, wherein deploying the occlusion device includes radially expanding the occlusion device from the compressed state to an expanded state, and wherein, in the expanded state—
the occlusion device includes a plurality of radially extending regions,
individual ones of the radially extending regions include an apex that contacts the endoluminal wall of the blood vessel,
each of the apices has a thickness along the longitudinal axis of the occlusion device, and
the combined thicknesses of the apices is less than about 50% of a total length of the mesh structure along the longitudinal axis; and
maintaining the occlusion device in the expanded state at the target site in the blood vessel at least until blood flow through the occlusion device and the vascular lumen at the vascular site is occluded.

10. The method of claim 9 wherein, in the expanded state, each of the apices has an edge radius that is between 0.10 mm and 0.40 mm.

11. The method of claim 9 wherein advancing the occlusion device includes advancing the occlusion device through a catheter via a pusher, and wherein the method further comprises detaching the occlusion device from the pusher.

12. The method of claim 9 wherein, in the expanded state, adjacent pairs of the radially extending regions are separated by a distance that inhibits laminar blood flow therebetween.

13. The method of claim 9 wherein—
individual ones of the radially extending regions (a) are substantially symmetric about a plane extending through the apex and perpendicular to the longitudinal axis and (b) have a circular cross-sectional shape along the plane,
the mesh structure is constrained by the blood vessel such that the expanded state is a partially-expanded state,
the mesh structure is further configured to radially expand to a fully-expanded state when the mesh structure is unconstrained by the blood vessel,
in the fully-expanded state, individual ones of the radially extending regions define a first angle relative to the longitudinal axis,
in the partially-expanded state, individual ones of the radially extending regions define a second angle relative to the longitudinal axis, and
the second angle is between about 20°-60° less than the first angle.

14. A method for embolizing a blood vessel having an endoluminal wall defining a vascular lumen, the method comprising:
advancing an occlusion device through a catheter, in a compressed state, to a target site in the vascular lumen of the blood vessel;
deploying the occlusion device at the target site in the blood vessel, wherein the occlusion device includes a mesh structure defining a longitudinal axis, wherein deploying the occlusion device includes radially expanding the occlusion device from the compressed state to an expanded state, and wherein, in the expanded state—
the occlusion device includes a plurality of radially extending regions,
individual ones of the radially extending regions include an apex that contacts the endoluminal wall of the blood vessel,
each of the apices has a thickness along the longitudinal axis of the occlusion device, and
the combined thicknesses of the apices is less than about 50% of a total length of the mesh structure along the longitudinal axis; and
maintaining the occlusion device in the expanded state at the target site in the blood vessel at least until the vascular lumen at the vascular site is embolized to occlude blood flow through the vascular lumen.

15. The method of claim 14 wherein individual ones of the radially extending regions (a) are substantially symmetric about a plane extending through the apex and perpendicular to the longitudinal axis and (b) have a circular cross-sectional shape along the plane.

16. The method of claim 14 wherein, in the expanded state, each of the apices has an edge radius that is between 0.10 mm and 0.40 mm.

* * * * *